US005491510A

United States Patent [19]
Gove

[11] Patent Number: 5,491,510
[45] Date of Patent: Feb. 13, 1996

[54] SYSTEM AND METHOD FOR SIMULTANEOUSLY VIEWING A SCENE AND AN OBSCURED OBJECT

[75] Inventor: Robert J. Gove, Plano, Tex.

[73] Assignee: Texas Instruments Incorporated, Dallas, Tex.

[21] Appl. No.: 161,831

[22] Filed: Dec. 3, 1993

[51] Int. Cl.⁶ .................................................. H04N 7/18
[52] U.S. Cl. ................................. 348/77; 348/45; 348/65; 345/8; 345/9
[58] Field of Search .................... 345/7–9; 348/45, 348/65, 77, 129, 130, 161; 359/631; H04N 7/18

[56] References Cited

U.S. PATENT DOCUMENTS

| | | | |
|---|---|---|---|
| 3,170,979 | 2/1965 | Baldwin et al. | 345/8 |
| 4,961,626 | 10/1990 | Fournier, Jr. et al. | 345/9 |
| 5,181,013 | 1/1993 | Bagshw et al. | 345/7 |
| 5,222,477 | 6/1993 | Lia | 348/45 |
| 5,227,769 | 7/1993 | Leksell et al. | 345/8 |
| 5,296,854 | 3/1994 | Hamilton et al. | 345/9 |
| 5,303,085 | 4/1994 | Rallison | 359/631 |

FOREIGN PATENT DOCUMENTS 2134298  8/1994  United Kingdom ........................ 345/8

OTHER PUBLICATIONS

Ryan, Michael, "Go Anywhere! But Don't Leave Your Chair," *Parade Magazine*, 21 Mar. 1993, pp. 18, 19, (Supplement to The Dallas Morning News).

*Primary Examiner*—Victor R. Kostak
*Assistant Examiner*—Cheryl Cohen
*Attorney, Agent, or Firm*—Charles A. Brill; James C. Kesterson; Richard L. Donaldson

[57] ABSTRACT

A visual information system to capture an input image using a camera 22, manipulate the image using processor 28, and project the processed image using optics 33 to superimpose the processed image on the actual object being observed by a viewer. Processing is done in real-time to allow the viewer to see both the actual and processed images while the viewer moves and changes viewing angles. Areas of interest in the displayed image may be highlighted or include graphical information for the viewer.

21 Claims, 2 Drawing Sheets

B.P. 110/70
H.R. 83
E.T. 5:38
OBJ. TO NERVE 2mm 5,491,510

SYSTEM AND METHOD FOR SIMULTANEOUSLY VIEWING A SCENE AND AN OBSCURED OBJECT

FIELD OF THE INVENTION

This invention relates to the field of image processing systems, more particularly to head-mounted image processing and display systems.

BACKGROUND OF THE INVENTION

There are many instances when it is advantageous to use photographs or electronically stored images to aid a viewer in observing the features and spatial relationships of an object. The features the viewer would like to locate or see are sometimes obscured or are difficult to locate with the unaided eye.

One example is during a surgical procedure. A surgeon may take a photograph or an electronic image of an area before surgery begins. The image may be from previous diagnostic tests such as magnetic resonance imaging (MRI) or computerized axial tomography (CAT). The surgeon will refer to this image during surgery as a guide for the procedure. For example, an image may be taken of a tumor before starting a removal procedure. During the procedure, the surgeon can refer back to the image to assist in locating the tumor or to ensure that the entire tumor has been removed.

SUMMARY OF THE INVENTION

The present invention provides a method and device for providing visual information to a viewer without blocking the vision of the viewer or requiring the viewer to look away from the object of interest. One embodiment of the invention provides an imaging system that displays a computer generated image in the field of view of the user, without obstructing the user's view of the object. This allows the user to see the image without looking away from the object of interest. Furthermore, the image will be manipulated to have the same perspective or viewpoint as the object from the user's perspective or viewpoint. The computer generated image may be superimposed on the view of the object that the user sees to help the user correlate information from the computer generated image with the user's actual view of the object.

It is a further advantage of the invention that the movement of the user or object can be monitored by the system and the computer generated images can be changed to compensate for the movement. This allows the user to view the computer generated image from different perspectives by simply moving his head. This three dimensional effect is important in that the image may show internal features that may not be visible in the user's view of the object. For example, during a surgical procedure, locations of major arteries can be marked in the image to allow the surgeon to avoid them.

DETAILED DESCRIPTION OF THE PREFERRED EMBODIMENTS

There are several drawbacks associated with using stored images to assist a viewer in identifying objects in his view. First, the viewer must look away from the object of interest in order to see the stored images, interrupting the work being performed and breaking the viewers concentration. Second, the images presented to the viewer have a fixed perspective, that is the viewer cannot usually manipulate the viewpoint of the image. Depending on the circumstances, the image may be difficult to correlate with the perspective of the viewer. For example, when testing an electronic assembly, the image of a component to be probed or removed may not be of much help when the component is surrounded by a large number of very similar, or worse yet, identical components.

A much better solution is to superimpose the image on the object being viewed, in effect highlighting the features of interest in the object. There are many applications for the vision enhancement imaging system disclosed, for example, three dimensional information from the images used to guide the surgical procedure discussed above could be used to generate enhanced images and projected into the line of sight of the surgeon to allow the surgeon to see the images without having to look away from the patient.

Figure 1:
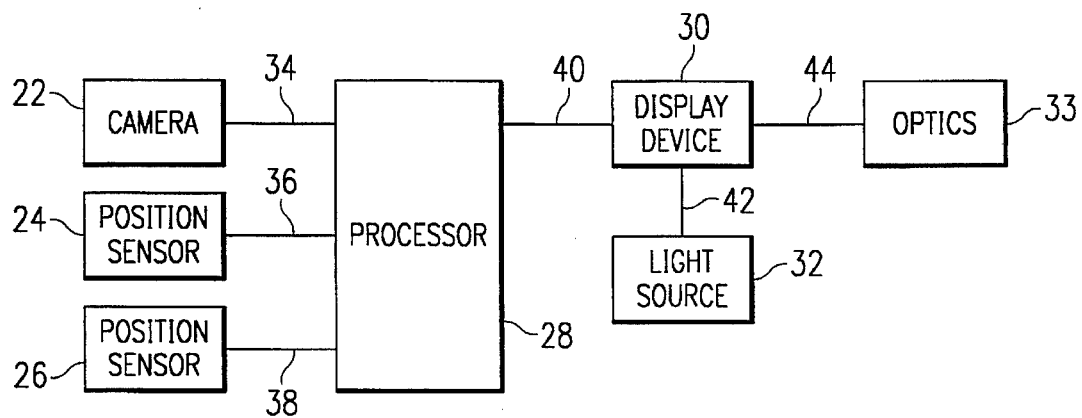
FIG. 1 is a schematic view of one embodiment of a visual information system.

FIG. 1 shows a schematic view of one embodiment of the disclosed imaging system. The video camera 22 monitors the subject, in this case a surgery patient, and transmits an electronic representation of the image to the processor 28 via channel 34. The choice of video camera depends on the information required and is not critical to the invention. For example, the camera could be monochrome or color, digital or analog, and could be receptive to light outside the visible spectrum. In some applications it may be advantageous to have more than one camera to provide the processor with additional perspectives to aid in the generation of three-dimensional images.

Optional patient position sensor 24 transmits information to the processor 28 to allow the image processing and display functions to compensate for patient motion. Note that the object position and motion information can be extracted from the image obtained via the camera and the use of vision algorithms. The processor 28 may determine position and motion information by tracking features of the patient. If no suitable features exist naturally on the patient, high contrast marks could be drawn on the patient prior to beginning a procedure to allow the patient to be tracked optically by the processor 28.

Viewer position sensor 26 tracks the position of the viewer to allow the viewer to move or turn to see different views of an image. Not only does the position sensor 26 allow the processor 28 to compensate for the viewing angle, it allows the processor 28 to scale the image as the distance from the object to the viewer changes and to move the image across the screen as the viewer scans the object. If the initial positions of the viewer and object are known, then motion sensors may be used instead of position sensors. Motion compensation prevents images from being warped or smeared as the patient moves.

The processor 28 applies image processing algorithms to manipulate the image from the camera 22 and other image sources. The other sources are not shown in FIG. 1, but could include scanned photographs, MRI or CAT scans, other medical diagnostic equipment, prior surgical procedures, or any image device. Image processing functions that would be desirable in some applications are image conditioning, feature extraction, and matching or correlation algorithms. The computer generated images may be wire-frame representations or fully rendered three-dimensional images or a hybrid combination of the two. For example, a tumor may be fully rendered and colorized while the surrounding tissue is represented by a wire-frame model. The processor could also use false coloring to highlight certain features or objects. Textual data may also be displayed to inform the surgeon of the patients vital signs, duration of surgery, etc.

In addition to manipulating the image data, the processor 28 may also receive inputs from the surgeon to allow the surgeon to mark areas of interest and to build a graphical database for later analysis. Inputs from the surgeon could also be used with stored information to aid feature recognition. The surgeon could use any available means to input data into the processor including a keyboard, mouse, touch screen, trackball, light pen, or voice recognition.

Processor 28 can be any type of processor or group of processors capable of performing the necessary image processing and display control functions required of the imaging system. For example, the processor could be designed around the Texas Instruments Multimedia Video Processor (MVP) image processing chip. The processor should have sufficient through-put to process the images, object motion, viewer position, and viewer input data in real-time. The required frame rate will vary depending on the application but should preferably be in the range of 60 to 100 frames per second, although 30 or fewer frames per second may be acceptable in some circumstances, especially situations with very little movement. The frame rate may be dynamically varied as image complexity and image processing algorithms vary the demands on processing power.

The processed images are sent to the display device 30 via display control bus 40. The display device could be any type of spatial light modulator capable of displaying an image such that it appears superimposed on an object being viewed. Optics 33 are used as required to focus and project the image. Light source 32 and optics 33 may not be required in all applications depending on the type of spatial light modulator used.

Figure 2:
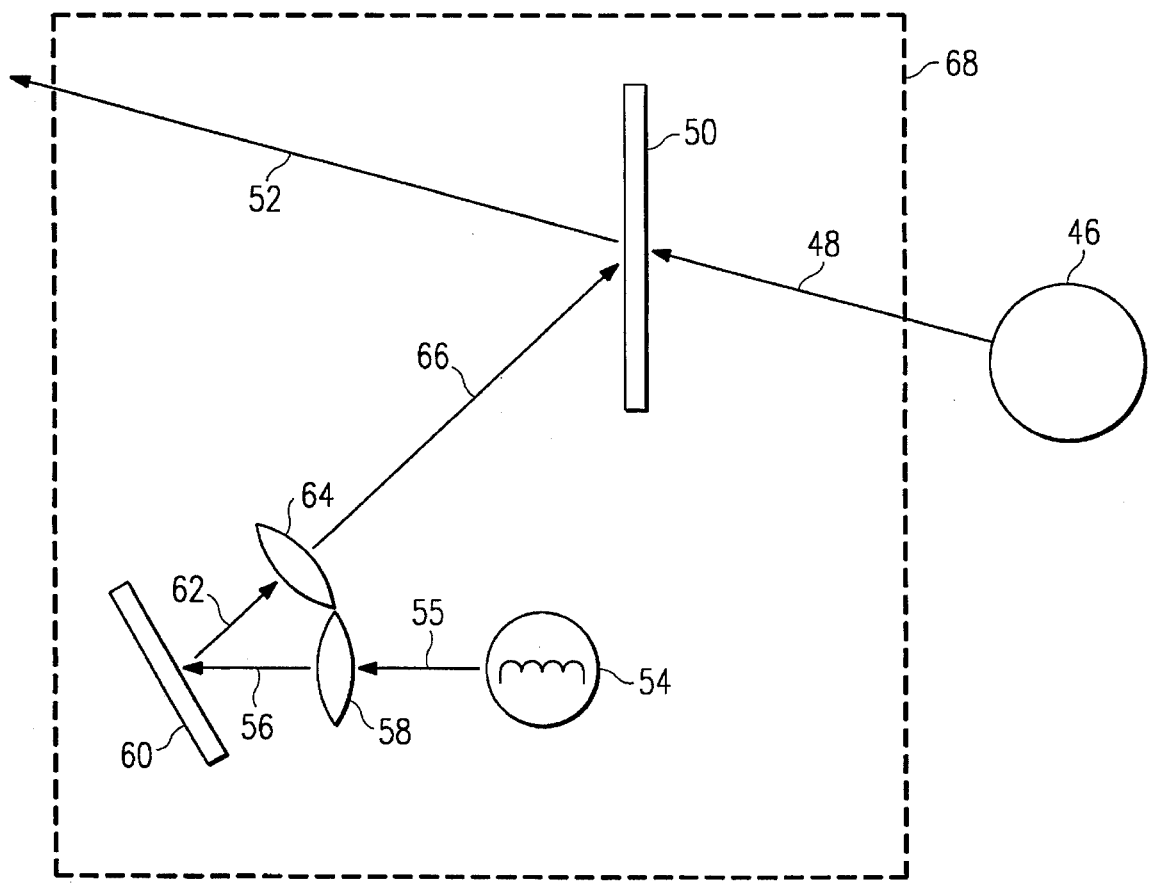
FIG. 2 is a schematic view of a first embodiment of a display mechanism of the visual information system.

One embodiment of a display system 68 comprising the display device, light source, and optics is shown in FIG. 2. Light from source 54 is focused and collimated as necessary by lens 58. The focused light 56 is modulated by a spatial light modulator, in this case a DMD array 60. The reflected light 62 is focused and magnified as necessary by lens 64. The light is then reflected by lens 50. At the same time, light 48 from the object 46 is allowed to pass through the lens 50. The light 52 from the object and the DMD array exits the display system 68 and is seen by the viewer.

The lens 50 may be worn like a pair of goggles, or a face shield, to allow the viewer to see the object 46 through the lens 50 and also see the image projected onto the lens. Lens 50 may be partially silvered to reflect light or may simply be any material with a partially reflective surface. Lens 50 is typically designed to allow approximately 90% of the light from the object to pass through the lens 50 while reflecting 10% of the reflected light 66 from the DMD. The amount of light reflected and transmitted by lens 50 depends on the application and the amount of light available from the object and the imager. The DMD 60 is particularly useful for this application because it allows the brightness of the projected image to be adjusted over a wide range. This wide adjustment allows the viewer to strike an acceptable balance between image brightness and object visibility.

Figure 3:
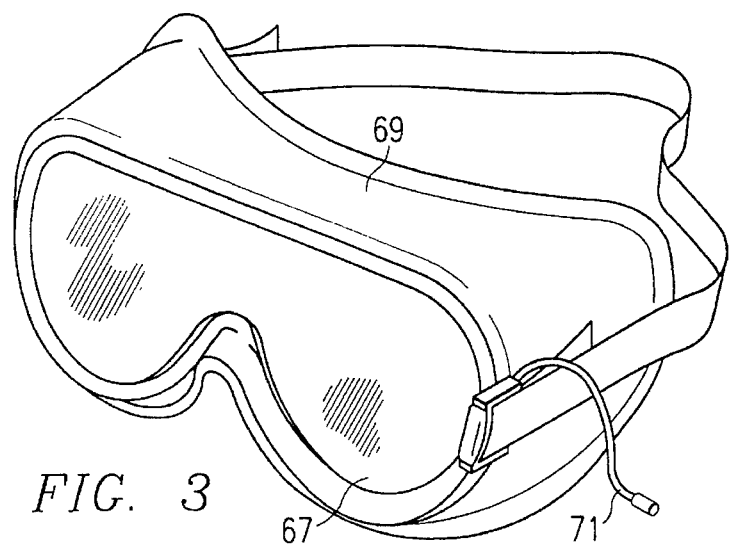
FIG. 3 is a pictorial view of a second embodiment of a display mechanism of the visual information system.

A second embodiment of a display system according to the present invention simply attenuates light from the object of interest. This second embodiment, shown in FIG. 3, may use a liquid crystal display (LCD) instead of a DMD. Because no light source or projection optics are required, the LCD 67 may be the actual lens of the goggles 69 worn by the viewer. Cable 71 carries the signals necessary to operate the LCD. The use of an LCD instead of the reflective lens of FIG. 2 attenuates more of the light from the image and reduces the visibility of the viewer. Areas of interest may be marked by attenuating light from the areas of interest, or by attenuating light from all areas except those of interest.

Figure 4:
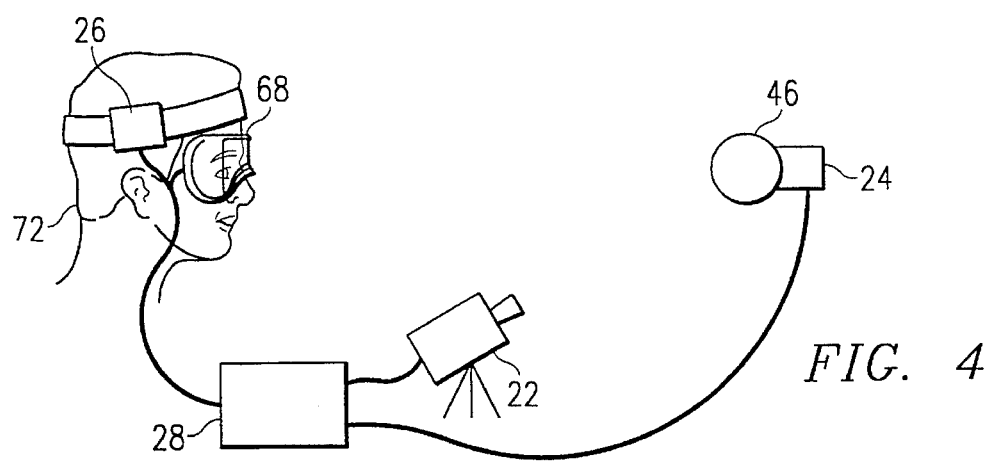
FIG. 4 is a pictorial view of one embodiment of the visual information system.

A pictorial view of one embodiment of the surgical imaging system is shown in FIG. 4. Viewer 72 looks though display system 68 at the object 46. In this embodiment both the display system 68 and the viewer position sensor 26 are head mounted on the viewer 72. Object position sensor 24 is attached to the object 46 without obstructing the view of either the viewer 72 or the camera 22. Processor 28 receives data from the camera 22, the viewer position sensor 26, and the object position sensor 24 and sends data to the display system 68.

Figure 5:
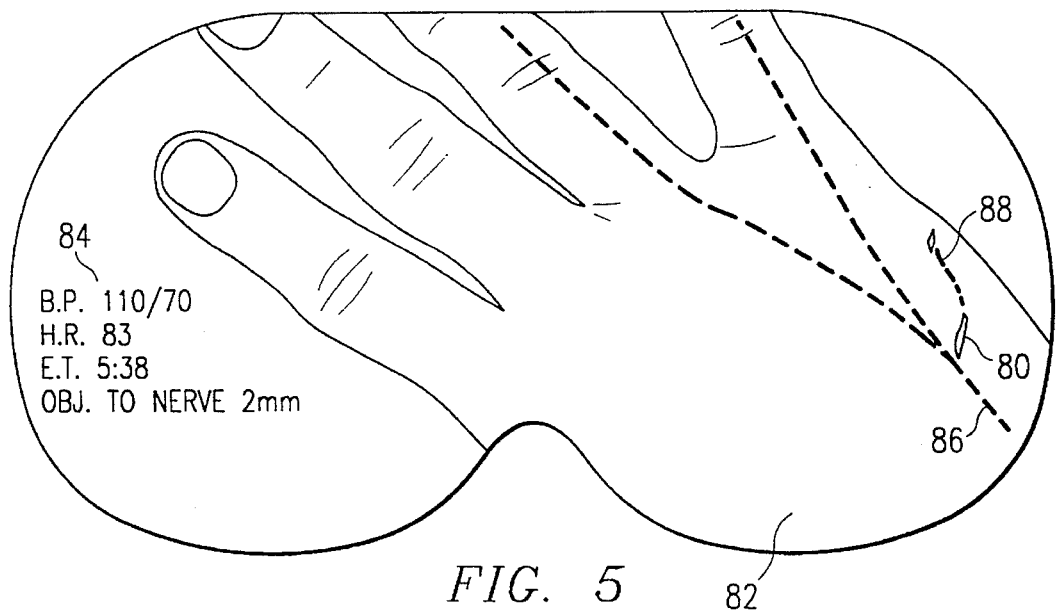
FIG. 5 is a pictorial view of a patients hand as seen through one embodiment of the disclosed visual information system.

FIG. 5 shows one example of the view through the imaging system during an operation to remove a foreign object from a patient. In FIG. 5 a surgeon is attempting to remove a foreign object 80 from a patient's hand 82. Textual information 84, such as the patient's vital signs, distances between objects, and elapsed time may be displayed. Objects of concern, in this case a nerve 86 that the surgeon is attempting to avoid, and the entrance path 88 of the object 80, may be highlighted. It should be appreciated that as the surgeon moves in relation to the patient, the perspective of the displayed image and the patient's hand will change in unison allowing the surgeon to determine the best method of removing the object 80.

Thus, although there has been disclosed to this point a particular embodiment for a surgical imaging system, it is not intended that such specific references be considered as limitations upon the scope of this invention except in-so-far as set forth in the following claims. Furthermore, having described the invention in connection with certain specific embodiments thereof, it is to be understood that further modifications may now suggest themselves to those skilled in the art, it is intended to cover all such modifications as fall within the scope of the appended claims.

What is claimed is:

1. An imaging system comprising:

a sensor for producing an output representative of the distance between a viewer and a first object and of the relative position and perspective of the viewer with respect to the first object in real-time;

facilities for storing information representative of an image of a second object including nonobservable portions thereof;

a processor responsive to said output for manipulating said information and for generating signals representing the image of the second object as having a distance from the viewer and a relative position and perspective to the viewer which is the same as the distance, relative position, and perspective applicable to the first object; and a display device for converting said signals into a virtual image and for permitting the viewer to simultaneously observe the first object and the virtual image.

2. The imaging system of claim 1, wherein said virtual image is superimposed on a direct view of said first object from the perspective of said viewer.

3. The imaging system of claim 1, wherein said virtual image is projected onto the lens of a pair of goggles.

4. The imaging system of claim 1, wherein said virtual image is projected onto a face shield.

5. The imaging system of claim 1 wherein said display device comprises a spatial light modulator, wherein said viewer looks through said spatial light modulator.

6. The imaging system of claim 1 wherein said display device comprises a digital micromirror device.

7. The imaging system of claim 1 wherein said display device comprises a liquid crystal display.

8. The imaging system of claim 1 wherein said display device comprises a partially silvered lens.

9. The imaging system of claim 1, wherein said display device is head-mounted on said viewer.

10. The imaging system of claim 1, wherein said processor manipulates said information in real-time.

11. The imaging system of claim 1, wherein said sensor is a camera for transmitting video information to said processor, said processor tracking features of said first object to determine the relative position of said viewer and said first object.

12. The imaging system of claim 1, wherein said sensor is at least one motion sensor in communication with said processor to allow said processor to compensate for the relative motion of said first object and said viewer.

13. The system of claim 1 wherein said display device converts said signals into a displayed image by attenuating light from said object.

14. The system of claim 1 wherein said virtual image is an image of an internal component of said first object.

15. The system of claim 1 wherein said viewer's direct view of said second object is blocked by said first object.

16. An imaging system comprising:

a means for determining and outputting position information regarding the relative position of a viewer and a first object;

an image source for providing image information from a stored image of a second object, wherein said second object is obscured from said viewer by said first object;

a processor for receiving said image and position information and for performing image processing routines on said image information and outputting an image signal in accordance with said position information; and a display device to receive said image signal and to convert said image signal into a displayed image, wherein said viewer may look through said display device and see the displayed image superimposed on a direct view of said first object.

17. The system of claim 16 wherein said second object is an internal component of said first object.

18. The system of claim 16 wherein said viewer's view of said second object is blocked by said first object.

19. A method of displaying an image of an object comprising:

tracking the relative position of a first object and a viewer;

processing a stored image of a second object to obtain an image signal representative of said second object from the perspective of said viewer from said first object, wherein said second object is obscured from said viewer by said first object;

converting said processed image signal into an image; and displaying said image such that said viewer sees said image superimposed on a direct view of said first object.

20. The method of claim 19 wherein tracking the relative position step comprises using at least one position sensor to track the relative position of said first object and said viewer.

21. the method of claim 19 wherein tracking the relative position step comprises using at least one position sensor to track the relative position of said first object and said viewer.

* * * * *